(12) United States Patent
Bimman

(10) Patent No.: US 6,921,404 B2
(45) Date of Patent: **\*Jul. 26, 2005**

(54) UNIVERSAL DEVICE AND METHOD FOR SUPPORTING BONES AND SURGERY TOOLS IN ORTHOPAEDIC SURGERY

(76) Inventor: Lev A. Bimman, 1031 Crestview Dr., Apt. 201, Mountain View, CA (US) 94040

( * ) Notice: Subject to any disclaimer, the term of this patent is extended or adjusted under 35 U.S.C. 154(b) by 402 days.

This patent is subject to a terminal disclaimer.

(21) Appl. No.: 10/302,381

(22) Filed: Nov. 25, 2002

(65) Prior Publication Data

US 2004/0102787 A1 May 27, 2004

(51) Int. Cl.[7] .............................. A61B 17/58; A61F 2/00
(52) U.S. Cl. ........................................................ 606/96
(58) Field of Search .............................. 606/53, 86, 87, 606/96, 98, 105, 54, 57; 403/24, 83–85, 103, 104, 110, 286, 300; 248/298.1, 505, 346.03

(56) References Cited

U.S. PATENT DOCUMENTS

| | | | | |
|---|---|---|---|---|
| 5,312,403 A | * | 5/1994 | Frigg ........................... | 606/54 |
| 5,601,551 A | * | 2/1997 | Taylor et al. ................. | 606/54 |
| 5,769,851 A | * | 6/1998 | Veith ........................... | 606/57 |
| 5,833,691 A | | 11/1998 | Bimman | |
| 6,030,387 A | * | 2/2000 | Ballier ......................... | 606/59 |
| 6,283,965 B1 | * | 9/2001 | Ballier ......................... | 606/59 |
| 6,309,392 B1 | * | 10/2001 | Alexander et al. ............ | 606/64 |
| 6,605,088 B1 | * | 8/2003 | St. Onge et al. .............. | 606/54 |
| 6,610,061 B2 | * | 8/2003 | Ballier ......................... | 606/59 |
| 6,730,086 B2 | * | 5/2004 | Hehli et al. ................... | 606/54 |

OTHER PUBLICATIONS

Orthopaedic Drill device "Smart Drive TM 6000 System" MicroAire Products, Co. (Canada).

\* cited by examiner

*Primary Examiner*—Eduardo C. Robert
*Assistant Examiner*—Anuradha Ramana

(57) ABSTRACT

A universal device for supporting bones and surgery tools in orthopaedic surgery consists of two rods supporting two spaced bone/tool holders installed in alignment to each other on opposite ends of the rods. The holders have V-shaped prisms with adjustable yokes for securing the broken bone part or a drilling tool in the respective prisms with a drill arranged coaxially to the facing bone part. One bone/tool holder is rigidly fixed to the rods, while the second holder slides relative to the fixed holder. The moveable holder is fixed between the nuts, e.g., for holding the parts of the broken bone in butt connection for growing together naturally. As compared to the known device of the same type, the device of the invention is light in weight, more universal in use, and is more simple in construction.

19 Claims, 6 Drawing Sheets

UNIVERSAL DEVICE AND METHOD FOR SUPPORTING BONES AND SURGERY TOOLS IN ORTHOPAEDIC SURGERY

FIELD OF INVENTION

The present invention relates to the field of surgery, and more particularly, to an apparatus and method for supporting both parts of a bone broken with an open fracture in a strictly aligned position for orthopaedic surgery. Such an alignment may be required for drilling coaxial holes in the bones to be connected by intramedullary nailing or for maintaining the bone parts in an aligned and butt-connected state until the bones grew up together naturally. The invention also relates to a method for supporting bones and surgical tools in orthopaedic surgery.

BACKGROUND OF THE INVENTION

A fracture is a complete or incomplete break in a bone resulting from the application of excessive force. An injury may be classified as a fracture-dislocation when a fracture involves the bony structures of any joint with associated dislocation of the same joint.

Fractures are also named by the specific portion of the bone involved and the nature of the break. The identification of the fracture line can further classify fractures. Types include linear, oblique, transverse, longitudinal, and spiral fractures. Fractures can be further subdivided by the positions of bony fragments and are described as comminuted, non-displaced, impacted, overriding, angulated, displaced, avulsed, and segmental.

Immobilization refers to the process of holding a joint or bone in place with a splint, cast, or brace. This is done to prevent an injured area from moving while it heals. All known apparatuses and processes for operations associated with connection of broken bones require the use of devices for immobilization, support and fixation of the broken bones or their parts. Supporting and fixing devices are needed for securing the broken parts of the bones together in connecting the bones through intramedullary nailing, extramedullary plates, as well as when there are chances for the broken bones to grow together naturally.

Intramedullary nailing or fixation is a method for holding a fractured bone in proper alignment by means of a metal pin or nail in the marrow cavity. This is normally performed by means of a steel spike inserted through the medually canal of a tubular bone to provide internal immobilization of fractures. Usually, intramedullary nailing fixation is utilized when there are no chances for the broken bones to grow together naturally.

In the opinion of specialists, for weight-bearing bones, intramedullary nailing is a fixation method superior to plates or external fixation, because the location of the rod in the intramedullary canal virtually guarantees proper axial alignment. Properly applied, an intramedullary fixation holds a fracture so securely that the patient can begin to move at once. It is an important factor, because, as is known, with early movements the fracture diseases (such as stiffness and edema) are abolished. Other advantages of the intramedullary fixation are precise reduction and immediate stability of the fractured bones.

But in spite of all the advantages of the intramedullary fixation, this method is used seldom and surgeons try to avoid the use of this method. This is because the intramedullary fixation requires a very accurate axial alignment of fractured bone parts, i.e., an accurate alignment of holes for the insertion of the intramedullary nail into the bone parts to be interconnected.

In accordance with conventional practice such a drilling has to be performed with the aid of an X-ray apparatus for locating the precise position of the hole of the intramedullary nail before the drilling operation is started. In any case, it is extremely difficult to ensure strictly coaxial position of the holes in both parts of the broken bones, and the applicant is not aware of any efficient devices which are on the market and which could provide an efficient and reliable axial alignment of holes in mating parts of the broken bone.

U.S. Pat. No. 5,833,691 granted to the same applicant in 1998 discloses a device for coaxially drilling holes in fractured bones for intramedullary fixation, which consists of a frame supporting a first V-shaped support for a first part of a fractured bone and a second V-shaped support for a second part of the fractured bone. The V-shaped supports are spaced from each other. The apparatus has a drilling head with a calibrated pin at the rear side of the drilling head. The drilling head is alternatingly installed in the aforementioned V-shaped supports for drilling coaxial and strictly aligned holes in both parts of the fractured bone. The calibrated pin has the same diameter as the drill bit of the drilling head and is intended for insertion into the bone hole, which is drilled first in order to support and align the drilling head with the second part of the bone during drilling of the second hole. In operation, the surgeon supports the drilling head with one hand and performs the feed of the bone toward the drill with another hand.

A main disadvantage of the aforementioned device is a significant weight which does not allow to keep this device for fixation of the bones over the entire period of healing, i.e., until the bone parts grow together naturally or during intramedullary connection. The known construction is not only heavy but also inconvenient for use by the operation-room personnel. Furthermore, the device has a complicated design, which cannot be easily produced in small dimensions. The device of the aforementioned patent may have a limited practical application for connection mainly of femur bones and is not suitable for intramedullary connection of clavicle, humerus, radius, ulna, fibula, tibia, and other thin bones. Movement of the drill during formation of holes in the bones is complicated and inefficient. Furthermore, the known apparatus is not versatile and cannot be left in place after fixation of the bone for natural growing together in view of its heavy weight and large dimensions.

The method claimed in the aforementioned U.S. Pat. No. 5,833,691 also has a number of disadvantages, the main of which is that for drilling of the hole in the second part of the broken bone, it was necessary to insert the tail shaft of the drill head into the hole previously drilled in the bone. This is extremely undesired operation as it will load the broken bone with an additional weight. The second problem is that the second part of the bone should be pulled toward the rotating drill bit.

Furthermore, the known device cannot be attached to the bone parts and remain attached to the bone till complete healing. This is because the entire device should rest onto a support surface.

OBJECTS AND SUMMARY OF THE INVENTION

It is an object of the invention to provide a universal device for supporting parts of broken bones and surgical tools in orthopaedic surgery, which is simple in construction, inexpensive to manufacture, easy to use, universal in application, light in weight, and suitable for use in intramedullary connection as well for holding the parts of broken bones for growing together naturally until complete healing. It is another object to provide a method for supporting bone and surgical tools in orthopaedic surgery, which makes it possible to drill holes in the broken bone parts without any insertion of the tail shaft of the drill into the opening drilled in the bone. It is another object to provide a method of supporting and naturally growing the parts of the broken bone to complete healing with the use of a small and lightweight universal device which is also used for alignment and guiding of a surgical drill. Still another object is to provide the aforementioned method in which drilling is always carried out by feeding the holder with the drill while the holder with the bone remains stationary.

A supporting device consists of two rods supporting two spaced bone/tool holders installed in alignment to each other on opposite ends of the rods. The holders have aligned V-shaped prisms and are provided with adjustable yokes for securing the broken bone part or a drilling tool in the respective prisms with a drill arranged coaxially to the facing bone part. One bone/tool holder is rigidly fixed to adjacent ends of the rods, while the second holder has a sliding fit over the threads on the opposite ends of the rods. The freedom of movement or fixation of the position of the second holder are determined by positions of two nuts screwed onto the threaded ends of the rods. The moveable holder is fixed between the nuts, e.g., for holding the parts of the broken bone in butt connection for growing together naturally. In the case of intramedullary fixation, a moveable bone/tool holder and the stationary holder participate in a relative motion with the amount of feed determined by the freedom of movement between the aforementioned nuts. The holders can be used for securing parts of the broken bones, or securing a surgery tool, e.g., a drill head, in one of the holders and a bone part in the other holder. For fixing the item in the holder, the holder is provided with an adjustable yoke. As compared to the known device of the same type, the device of the invention is light in weight, more universal in use, and is more simple in construction.

DETAILED DESCRIPTION OF THE INVENTION

Figure 1:
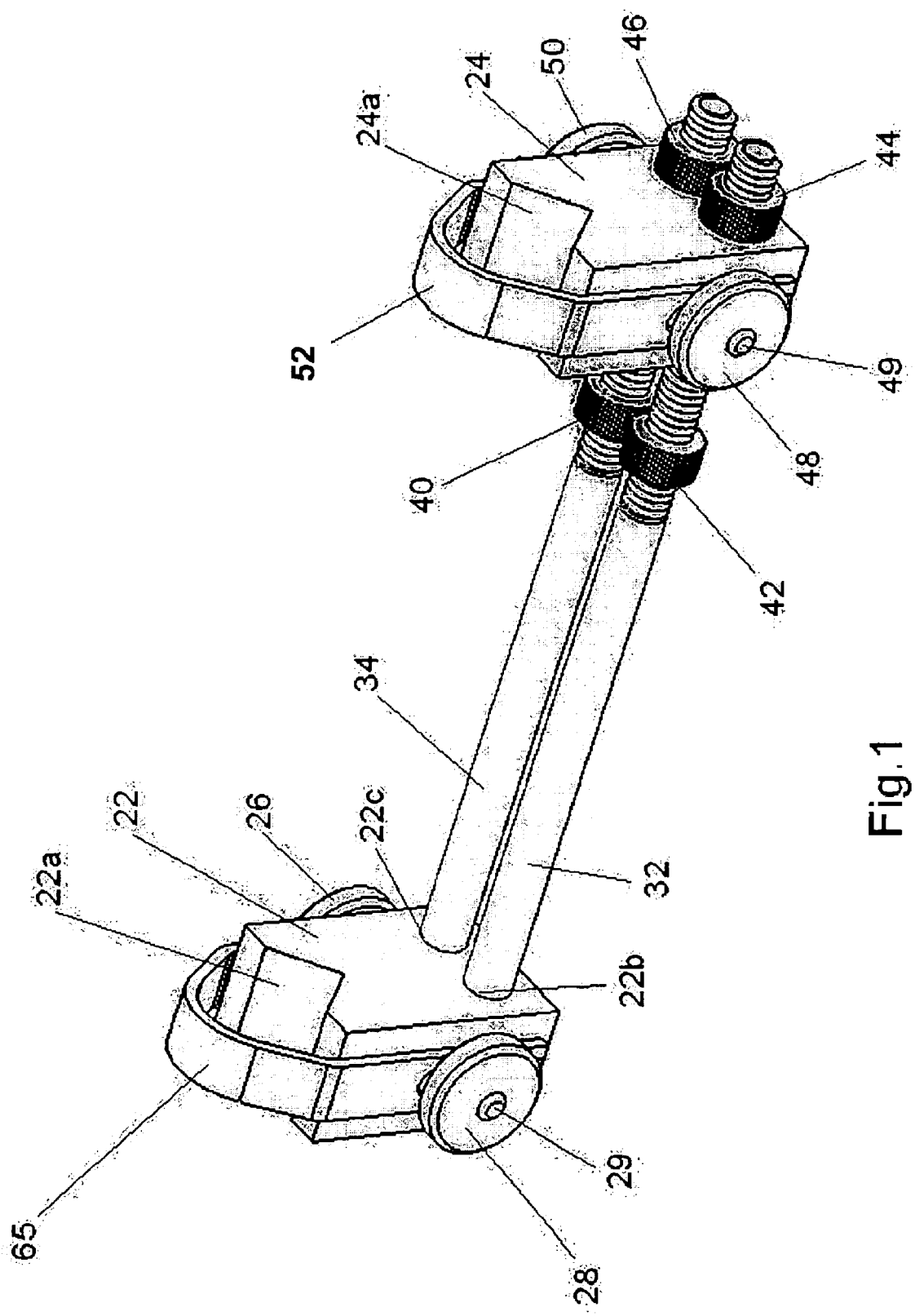
FIG. 1 is a general three-dimensional view of an apparatus of the invention.
Figure 2:
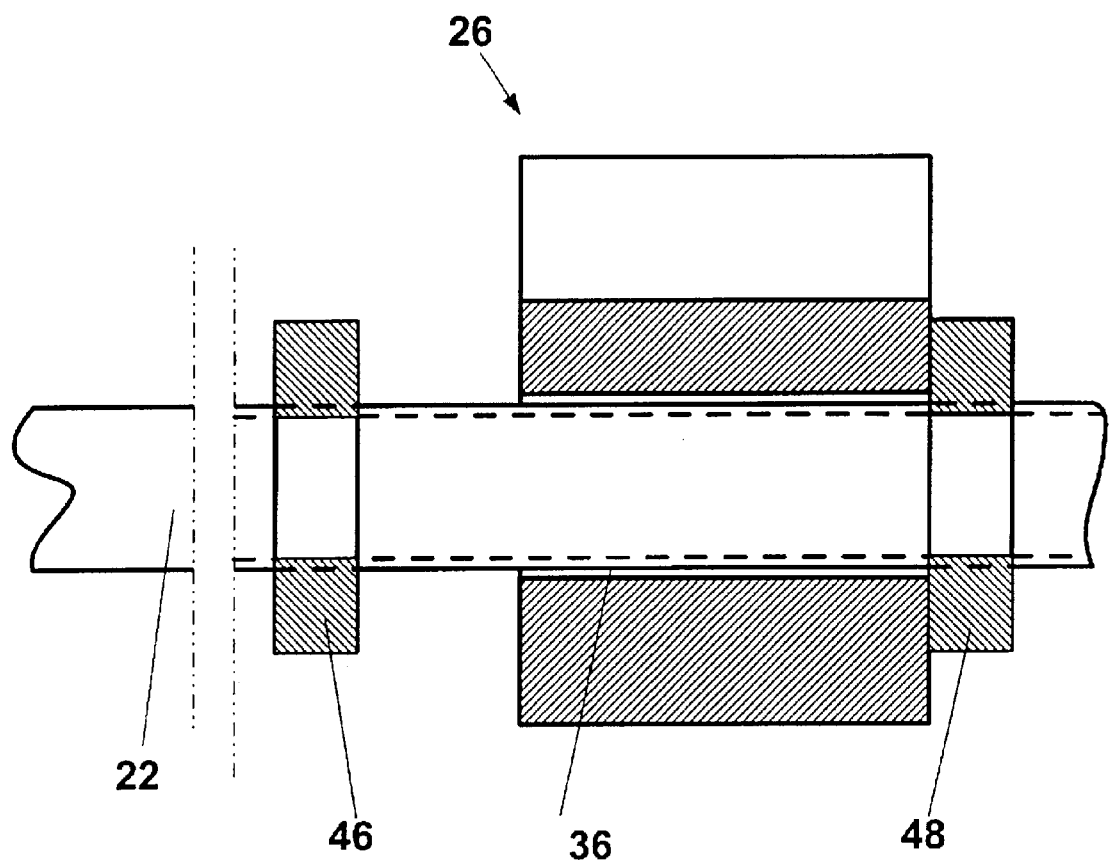
FIG. 2 is a sectional view along the line 11—11 of FIG. 1.

The apparatus of the invention is shown in FIG. 1, which is a general three-dimensional view of the apparatus. The apparatus as a whole is designated by reference numeral 10. It consists of two rods 20 and 22 that support two spaced bone/tool holders (hereinafter referred to simply as "holders") 24 and 26 installed in alignment to each other on opposite ends of the rods 20 and 22. The holder 24 has on its upper surface a V-shaped prism 28, and the holder 26 has on its upper surface a V-shaped prism 30, which is aligned with the position of the prism 28. It is understood that the term "upper" is conventional as the device can be used in any convenient spatial position. Therefore the term "upper" relates to the position of the prism in FIG. 1, and strictly speaking the prisms are formed in the surfaces of the holders opposite to holes formed in the holder for connection with the rods 20 and 22. For this connection, holes 32, 34 are formed in the holder 24 for rigid connection of the rods 32 and 34 to the holder 24, e.g., by pressure fit, while holes, such as a hole 36 shown in FIG. 2, which provides a sliding fit of the holder 26 on the rod 20, are formed in the holder 26. Although only one such hole 36 is seen in FIG. 2, which is a sectional view along the line II—II of FIG. 1, it is understood that a similar hole is provided in the holder 26 for the rod 22.

The ends of the rods 20, 22 opposite to the end that rigidly supports the holder 24 have threaded portions with threads 38 and 40. The threaded ends of the rods 20 and 22 support the holder 26 moveably, e.g., with a sliding fit of the rods in the hole, such as the hole 36 (FIG. 2). For this purpose, the diameter of the holes, such as the hole 36, is slightly greater that the outer diameter of the threads, such as the thread 38. The freedom of movement of the holder 26 with respect to the rods 20, 22 and hence to the fixed holder 24 is limited by the positions of nuts 42,44 screwed onto the thread 38 on the rod 20 and nuts 46 and 48 screwed on the thread 40 on the rod 22.

Each holder is equipped with fixing means for securing the aligned broken bone parts or a surgical tool in combination with an aligned bone part in the respective prisms. In the embodiment shown in FIG. 1 such fixing means are made in the form of an adjustable yoke for clamping on the holder 24 and an adjustable clamping yoke 52 on the holder 26. Each yoke 50 and 52 comprises a flexible U-shaped strip with longitudinal slots, such as slots 54 and 56 seen on the holders 24 and 26, respectively. It is understood that similar slots are provided on other sides of the yokes 50 and 52, invisible in FIG. 1. Inserted into respective slots are ends of threaded pins 58 and 60 rigidly fixed in the side surfaces of the holders 24 and 26, respectively. Similar pins, which are not seen in FIG. 1, are provided on the opposite sides of the holders 24 and 26. The ends of the threaded pins, such as pins 58 and 60, protrude from the surfaces of the yokes to the length sufficient for screwing nuts, such as nuts 62a, 62b and 64a, 64b for fixing the ends of the U-shaped yokes in position required for clamping the items inserted into the spaces formed between the yokes 50, 66 and respective prisms 28, 30. The nuts 62a, 62b and 64a, 64b may have a round shape with knurling on the peripheral surface, as shown in FIG. 1.

Figure 3:
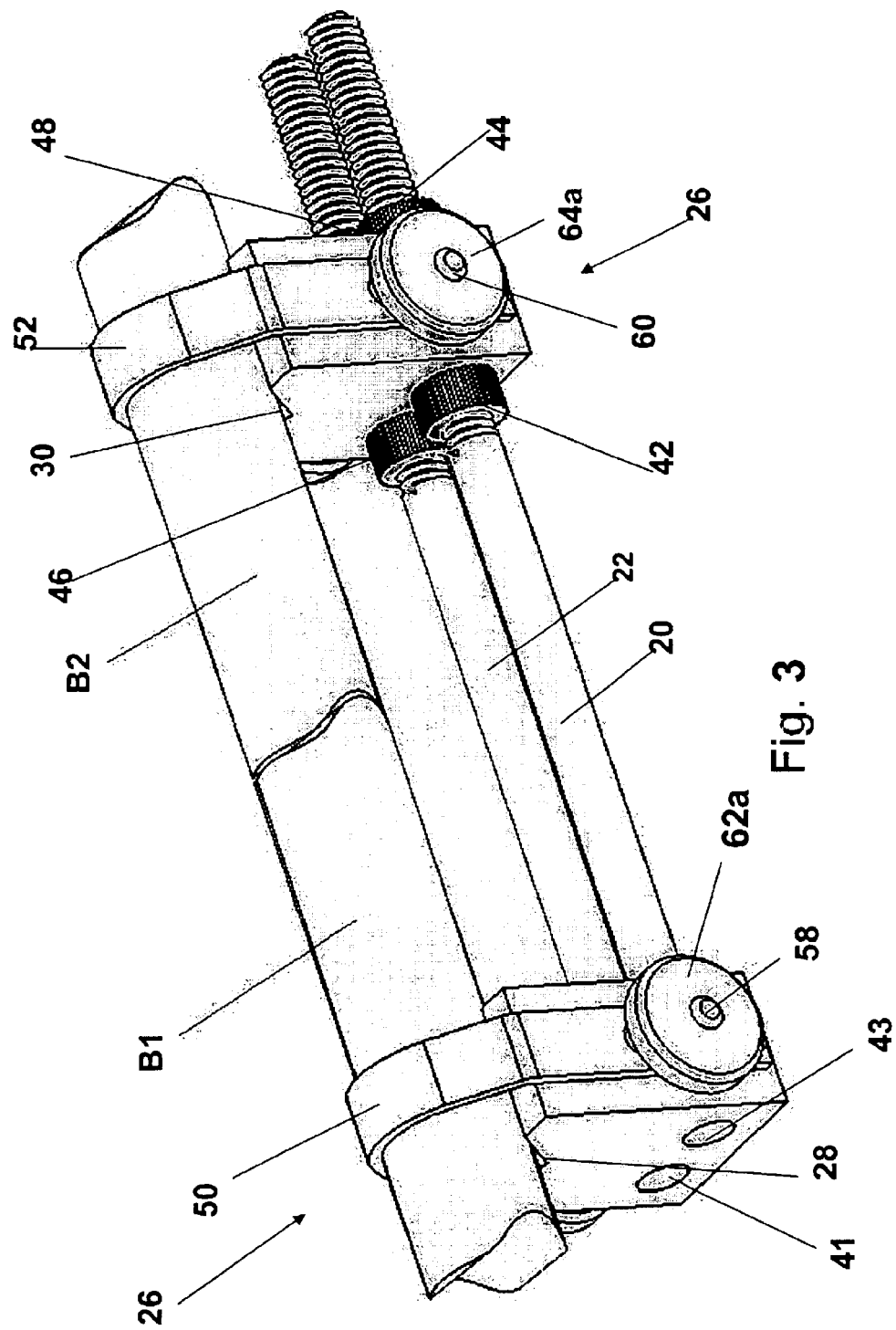
FIG. 3 is a view similar to FIG. 1 illustrating the apparatus that supports aligned broken parts of the bone fixed in the apparatus in a position for growing together naturally.

FIG. 3 is a three-dimensional view of the apparatus 10 of FIG. 1 with two parts B1 and B2 of a bone broken with an open fracture and inserted into the holders 24 and 26, respectively. Such an arrangement can be used for bone parts, which have a chance to grow together naturally. Each bone part is placed into a respective holder, e.g., the bone part B1 is placed into the prism 28 (FIGS. 1 and 3) of the holder 24, and the bone part B2 is placed into the prism 30 of the holder 26 in a position aligned with respect to the bone part B1. Both bone parts B1 and B2 are brought together in butt connection shown in FIG. 3 with exact alignment and matching of the bone part ends, and then both parts B1 and B2 are pressed towards each other with the force required by the medical procedure and are fixed in a mutually pressed state with the use of the clamping yokes 50 and 52 tightened by nuts 62a, 62b and 64a, 64b, respectively (FIG. 1 and FIG. 3). The device may remain in the condition shown in FIG. 3 until complete healing, i.e., when the bone parts B1 and B2 grow together. It is understood that in this procedure the moveable holder 26 is also rigidly fixed with respect to the rods 20, 22 and with respect to the holder 24 by clamping the holder 26 between the nuts 42, 46 and 44, 48 in the adjusted operative position, as shown in FIG. 3. Reference numerals 41 and 43 in FIG. 3 show through holes that can be drilled in the holder 24 for insertion of the rods 20 and 22. If necessary, instead of the press fit, the rods 20 and 22 can be fixed in the holder 24 by the threaded pins, such as the aforementioned pin 58.

Figure 4:
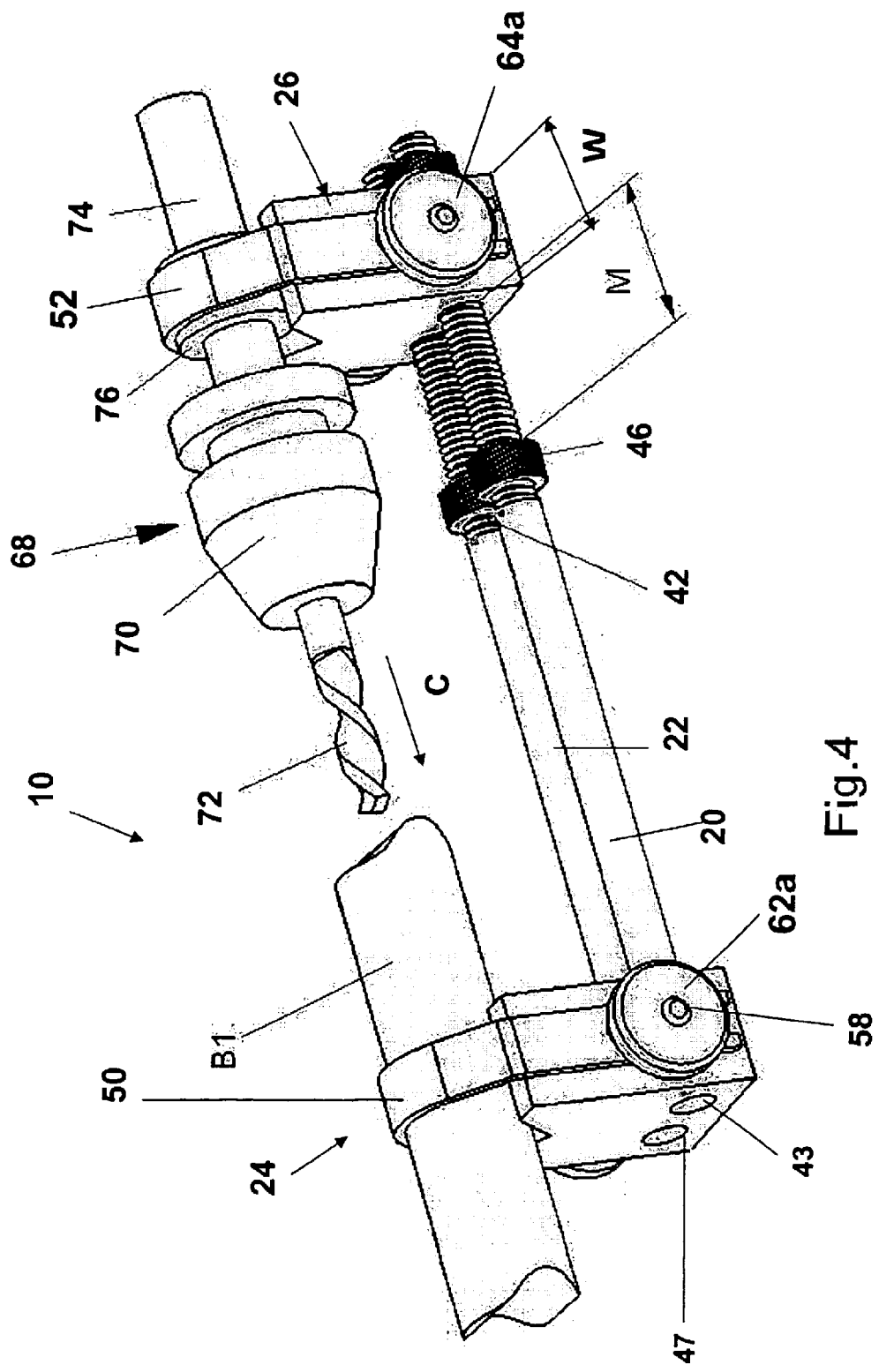
FIG. 4 is a view of an apparatus similar to FIG. 1 with a drill head installed in one of the bone/drill holders for drilling a hole in one of the parts of the broken bone for intramedullary connection.

FIG. 4 is a view of the apparatus 10 similar to FIG. 1 with a drill head assembly 68 installed in one of the holders, e.g., in the moveable holder 26, for drilling a hole in one of the parts, e.g., in part B1 of the broken bone for intramedullary connection. The drill head assembly may consist of a drill bit chuck 70 for clamping a drill bit 72 with a cylindrical tail shaft 74. The assembly 68 may be provided with a changeable guide ring 76 which, in the situation shown in FIG. 4 is clamped in the yoke 52 and is used for guiding the drill head assembly, when the latter is feed towards the bone part B1 in the direction of arrow C. A set of guide rings 76, which are slidingly fit onto the tail shaft 74 so that the tail shaft 74 can freely rotate in the ring, may consist of rings of different diameters. This makes it possible to select a proper ring to align the drill bit axis with respect to the axis of the bone B1 or B2. Drilling is carried out by fixing the tail shaft 74 in a chuck of a drive device, e.g., an electric drill (not shown), which is manually (or mechanically) moved in the direction of arrow C. An example of an electric drill suitable for use in conjunction with the apparatus of the invention is a SmartDrive 6000 System orthopaedic drill produced by MicroAire Products Co. in Canada.

The feed stroke M (FIG. 4), and hence the depth of the drilled hole, will be equal to the distance between the nuts 42, 46 and nuts 44, 48 minus the width W of the holder 26. The tail shaft 74 has a sliding fit in the guide ring 76 (FIG. 4). If necessary, the electric drill (not shown) and the drill head assembly 68 may remain stationary (with the drill bit 72 rotating), while feeding is carried out by moving the holder 24 with bone part B1 fixed in it in the direction opposite to arrow C in FIG. 4. It is understood that in this case the holder 24 will be moved together with the rods 20 and 22 guided in the openings 36, 37 of the holder 26 (FIGS. 2 and 4).

Figure 5:
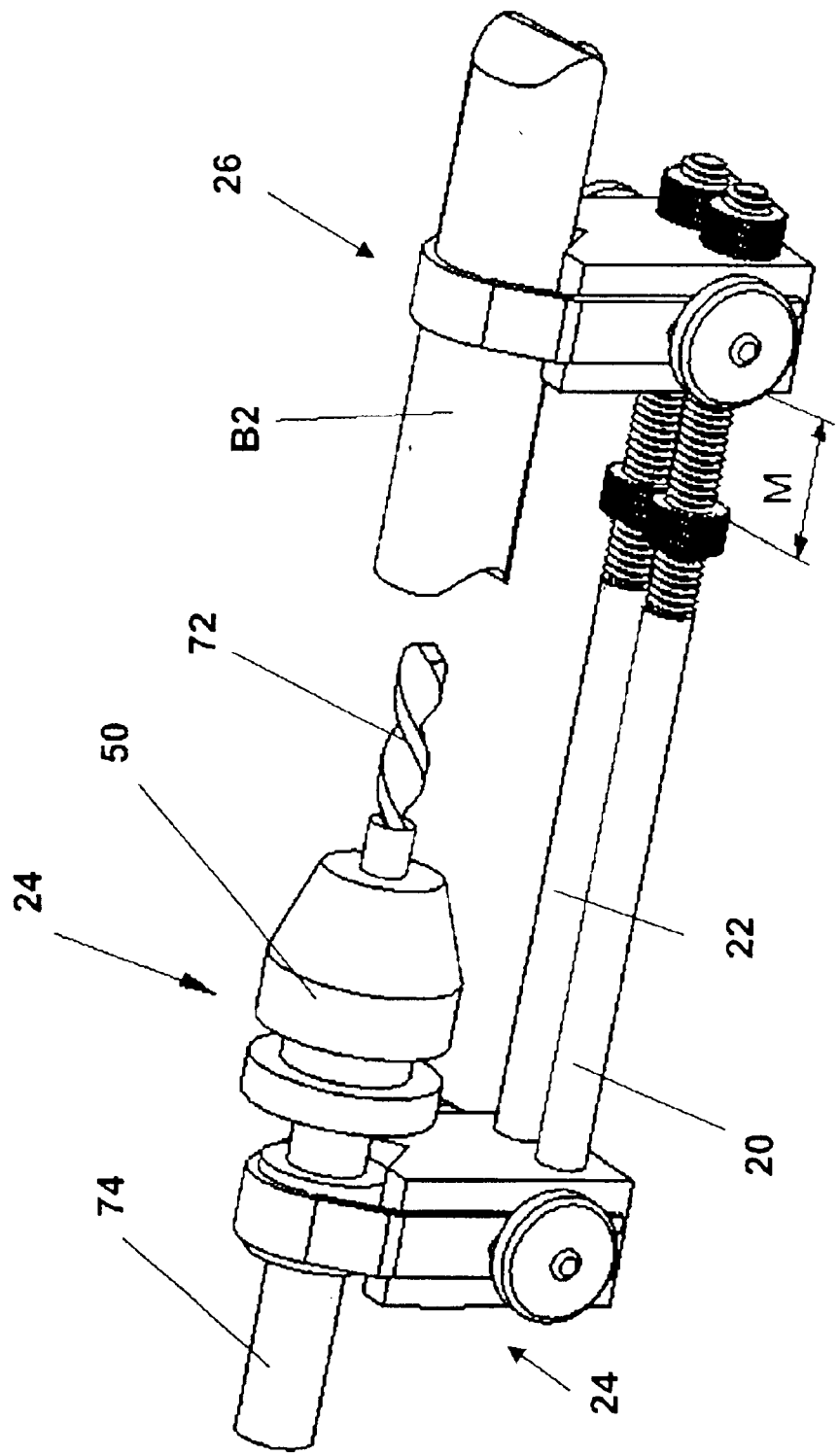
FIG. 5 is a view of an apparatus similar to FIG. 4 with the drill in a position for drilling a coaxial opening in the mating bone part.

FIG. 5 is a view of the apparatus 10 similar to FIG. 4 with the drill head assembly 68 in the position for drilling a coaxial opening in the mating bone part B2. After drilling of the hole in the bone part B1 is completed, the drill head assembly 68 and the guide ring 76 are released from the holder 26 by unclamping the U-shaped yoke 52. The second bone part B2 is inserted, preliminarily aligned with the position of the treated bone part B1, and clamped in the prism 30 (FIG. 1) of the holder 26. The drill head assembly 68 and the guide ring 76 are installed and fixed in the holder 24 in the aligned position with respect to the bone part 92. If the tail shaft 74 was disconnected from the electric drill (not shown), it is again inserted into the electric drill chuck, and a hole is drilled in the end face of the bone part B2 to the depth determined by the drill feed stroke M.

Further operations are carried out by the surgeon in accordance with the specified intramedullary connection procedure.

It is worth to note that in contrast to the device of U.S. Pat. No. 5,833,691, drilling of holes in both bone parts B1 and B2 for intramedullary connection with the use of the apparatus of the invention is carried out without any insertions of the drill head tail shaft 74 into the hole of the bone. Furthermore, drilling of holes in both bone parts B1 and B2 is performed by feeding the drill while the bone remains secured in its appropriate holder. These two features make the device and method of the present invention distinctively advantageous over the prior art device designed for the same purpose.

Figure 6:
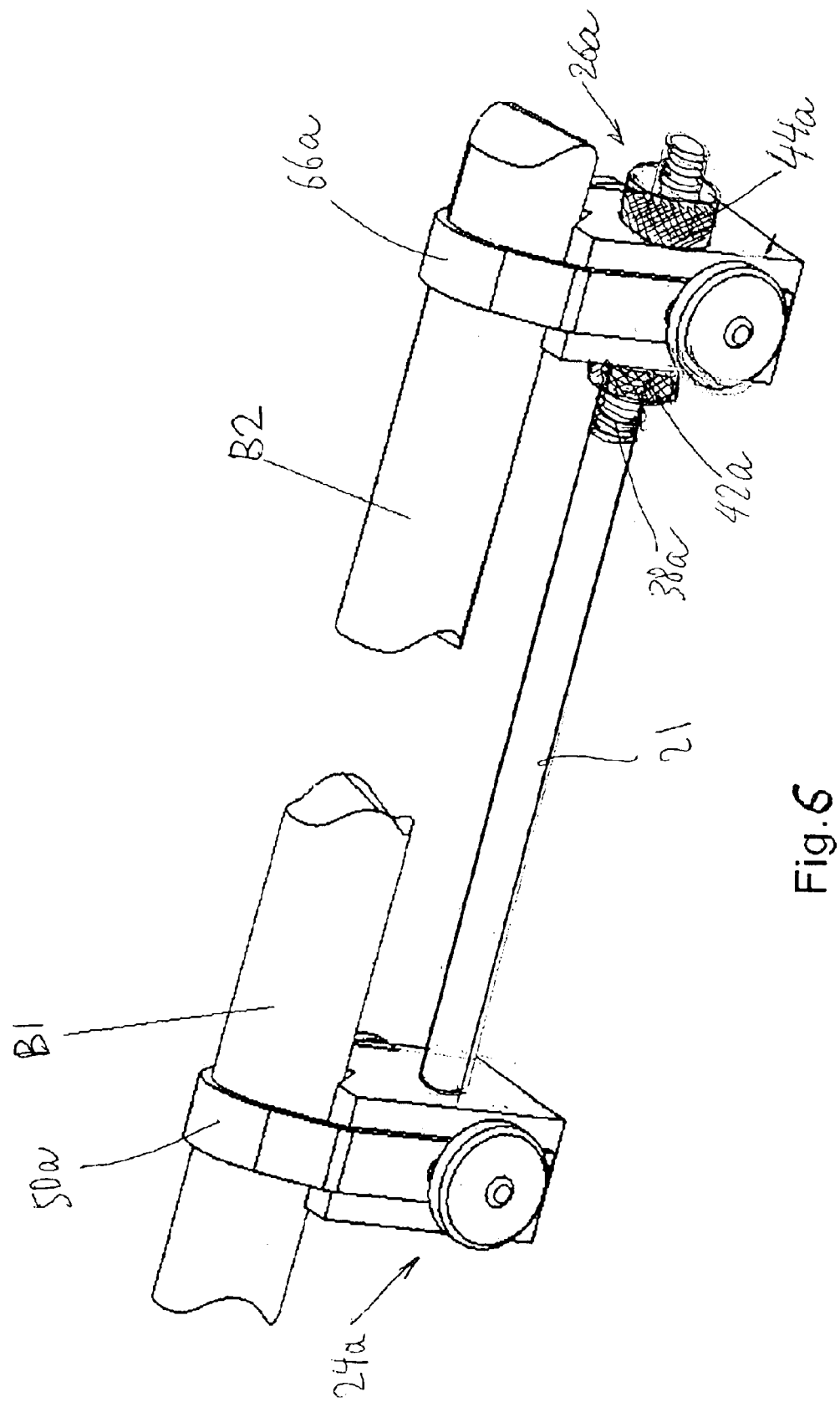
FIG. 6 is a view of an apparatus of the invention similar to the one shown in FIGS. 1 to 4 but with the use of a single rod for connecting the bone/drill holders.

FIG. 6 is a view of an apparatus of the invention similar to the one shown in FIGS. 1 to 4 but with the use of a single rod for connecting the bone/drill holders. In fact, the apparatus of this embodiment is substantially identical to the apparatus of the previous embodiment and differs from it only by the use of a single rod 21 for connecting the bone/drill holders 24a and 26a. The rod 21 has a thread 38a, and the holder 26a can be fixed or released for a limited movement by means of nuts 42a and 44a screwed onto the thread 38a.

The device of the embodiment shown in FIG. 6 operates in the same manner as the one described with reference to FIGS. 1 through 5.

The parts of the apparatus 10 shown and described with reference to FIGS. 1 through 6 can be made from a light biometrically compatible metal or metal alloy such as a stainless steel of a titanium alloy for sterilization and multiple use or can be made from a biometrically compatible plastic for making the apparatus disposable after a single use. The apparatus 10 of the invention can be made with overall dimensions much smaller than those of the known apparatus disclosed in the aforementioned U.S. Pat. No. 5,833,691.

Thus, it has been shown that the invention provides a universal device for supporting parts of broken bones and surgical tools in orthopaedic surgery, which is simple in construction, inexpensive to manufacture, easy to use, universal in application, light in weight, and suitable for use in intramedullary connection as well for holding the parts of broken bones for growing together naturally until complete healing.

The method of the invention makes it possible to drill holes in both bone parts by feeding the drill while the bone part remains secured in its appropriate holder. Furthermore, drilling of holes for intramedullary connection can be carried out with any undesired insertion of the drill head tail shaft into the hole drilled in the bone. The lightweight device of the invention is attached to the bone parts and may remain on the bones till complete healing, while the known device can support the bones only when it rests onto a support surface.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, the holders may have any other configuration different from the rectangular shape shown in FIGS. 1 through 5, e.g., they may be oval, round, square, or triangular. Semicircular grooves or groove having cross-section corresponding to the cross-sectional shape of the respective bone can be formed in the holders instead of the prisms. If necessary, profile inserts can be provided in the recesses of the holders for supporting the bones. The rods can be made integrally with one of the holders. The bones and tools can be clamped with removable C-shaped clamps, or the holders may have a vice-like construction with jaws of appropriate configuration. It is also obvious that only one rod that connects both holders can be used instead of two rods 20 and 22.

What is claimed is:

1. A universal device for supporting bones and surgery tools in orthopaedic surgery comprising:
    a first holder having a first supporting surface for supporting bones or surgery tools in oriented positions;
    at least one elongated member having means for rigidly securing said first holder;
    a second holder spaced from said first holder and movably supported by said at least one elongated member, said second holder having a second supporting surface for supporting bones or surgery tools in oriented position, said second supporting surface being aligned with said first supporting surface;
    first clamping means installed on said first holder for clamping said bones or tools in said first holder in said oriented positions;
    second clamping means installed on said second holder for clamping bones or tools in said second holder in said oriented positions; and
    adjustable stopper means for limiting movements of said second holder on said at least one elongated member;
    said support surface in each of said first holder and said second holder being a V-shaped prism surface, and said at least one elongated member being a rod having at least one threaded end.

2. The universal device of claim 1, wherein said adjustable stopper means comprise at least two nuts screwed onto said threaded end, said second holder being slidingly installed on said threaded end between said at least two nuts.

3. The universal device of claim 1, wherein said first clamping means and said second clamping means each comprises a U-shaped yoke with means for adjusting and securing the position of said U-shaped yoke relative to either of said first holder or said second holder.

4. The universal device of claim 3, wherein said means for adjusting and securing position of said U-shaped yoke comprises a threaded pin rigidly attached to said respective holder, a slot in said U-shaped yoke through which said threaded pin protrudes, and a nut for screwing onto a protruding end of said threaded pin.

5. The universal device of claim 4, further provided with a drilling head unit which can be interchangeably clamped in said first support surface and said second support surface, said drilling head having a drill chuck for clamping a drill bit, a tail shaft for clamping in a drive device, and a replaceable guide ring slidingly fit onto said tail shaft, said replaceable guide ring having the ability of being placed onto a respective support surface selected from said first supporting surface and said second supporting surface and can be clamped by a clamping means selected from said first clamping means and said second clamping means.

6. A universal device for supporting bones and surgery tools in orthopaedic surgery comprising:
    a first holder having a first supporting surface for supporting bones of surgery tools in oriented positions;
    two elongated members having means for rigidly securing said first holder;
    a second holder spaced from said first holder and movably supported by said two elongated members, said second holder having a second supporting surface for supporting bones and surgery tools in oriented position, said second supporting surface being aligned with said first supporting surface;
    first clamping means installed on said first holder for clamping said bones and tools in said first holder in said oriented positions;
    second clamping means installed on said second holder for clamping bones or tools in said second holder in said oriented positions;
    adjustable stopper means for limiting movements of said second holder on said elongated means; and
    a drilling head unit which can be interchangeably clamped in said first support surface and said second support surface;
    said drilling head comprising a drill chuck for clamping a drill bit, a tail shaft for clamping in a drive device, and a replaceable guide ring slidingly fit onto said tail shaft, said replaceable guide ring having the ability of being placed onto a respective support surface selected from said first supporting surface and said second supporting surface and can be clamped by a clamping means selected from said first clamping means and said second clamping means.

7. The universal device of claim 6, wherein said support surface in each of said first holder and said second holder is a V-shaped prism surface.

8. The universal device of claim 7, wherein each of said two elongated members comprises a rod having at least one threaded end.

9. The universal device of claim 7, wherein said adjustable stopper means comprise at least two nuts screwed onto said threaded end, said second holder being slidingly installed on said threaded end between said at least two nuts.

10. The universal device of claim 7, wherein each of said two elongated members comprises a rod having at least one threaded end.

11. The universal device of claim 10, wherein said adjustable stopper means comprise at least two nuts screwed onto said threaded end, said second holder being slidingly installed on said threaded end between said at least two nuts.

12. The universal device of claim 11, wherein said first clamping means and said second clamping means each comprises a U-shaped yoke with means for adjusting and securing position of said U-shaped yoke relative to a respective holder selected from said first holder and said second holder.

13. The universal device of claim 12, wherein said means for adjusting and securing position of said U-shaped yoke comprises a threaded pin rigidly attached to said respective holder, a slot in said U-shaped yoke through which said threaded pin protrudes, and a nut for screwing onto a protruding end of said threaded pin.

14. The universal device of claim 10, wherein said first clamping means and said second clamping means each comprises a U-shaped yoke with means for adjusting and securing position of said U-shaped yoke relative to a respective holder selected from said first holder and said second holder.

15. The universal device of claim 14, wherein said means for adjusting and securing position of said U-shaped yoke comprises a threaded pin rigidly attached to said respective holder, a slot in said U-shaped yoke through which said threaded pin protrudes, and a nut for screwing onto a protruding end of said threaded pin.

16. A method for supporting bones and surgical tools in orthopaedic surgery comprising:

providing a universal device comprising at least one elongated member, a stationary holder rigidly fixed to said at least one elongated member, a moveable holder spaced from said stationary holder and moveably installed on said at least one elongated member, adjustable means on said at least one elongated member for fixation or limited guided movement of said moveable holder on said at least one elongated member, aligned support surfaces on said stationary holder and said moveable holder, and replaceable alignment means for supporting a surgical drilling tool in one of said stationary holder and moveable holder in an aligned position with respect to one part of said broken bone supported in the other of said holders;

installing and fixing one part of a bone broken with an open fracture on said support surface of one of said stationary holder and said moveable holder;

installing and fixing a surgical drilling tool in said replaceable alignment means and in said aligned position on said support surface of the other of said stationary holder and said moveable holder;

drilling a hole in said one part of the bone broken with an open fracture by moving said moveable holder towards said one part of the bone to a depth required for intramedullary connection;

moving said moveable holder away from said one part of the bone upon completion of drilling;

disconnecting and removing said one part of the bone from said one of said stationary holder and said moveable holder;

disconnecting said surgical drilling tool together with said replaceable alignment means from other of said stationary holder and said moveable holder;

installing and fixing said other part of the bone broken with an open fracture on said support surface of the other of said stationary holder and said moveable holder;

installing and fixing a surgical drilling tool in said replaceable alignment means and in said aligned position on said support surface of said one of said stationary holder and said moveable holder;

drilling a hole in said other part of a broken bone with an open fracture by moving said moveable holder towards said other part of the bone to a depth required for intramedullary connection;

moving said moveable holder away from said other part of the bone upon completion of drilling; and completing said intramedullary connection.

17. The method of claim 16, wherein said drilling surgical tool has a tail shaft, said replaceable alignment means comprising replaceable rings of different diameters, and said support surfaces comprising V-shaped prisms.

18. The method of claim 17, wherein said adjustable means on said at least one elongated member for fixation or limited guided movement of said moveable holder on said at least one elongated member comprise a threaded end of said at least one elongated member and two nuts screwed onto said threaded ends on both sides of said moveable holder.

19. A method for supporting bones in orthopaedic surgery comprising:

providing a universal device comprising at least one elongated member, a stationary holder rigidly fixed to said at least one elongated member, a moveable holder spaced from said stationary holder and moveably installed on said at least one elongated member, adjustable means on said at least one elongated member for fixation or limited guided movement of said moveable holder on said at least one elongated member, aligned support surfaces on said stationary holder and said moveable holder;

installing and fixing one part of a bone broken with an open fracture on said support surface of one of said stationary holder and said moveable holder;

installing and fixing the other part of said bane broken with an open fracture on said support surface of the other of said stationary holder and said moveable holder;

aligning said one part of the bone and said other part of the bone with respect to each other, and fixing them in aligned positions;

moving said moveable holder towards said stationary holder until said one part of said bone and said other part of bone are connected in a butt connection in said aligned positions;

fixing said moveable holder by said adjustable means while maintaining said bone parts under conditions of said butt connection; and maintaining said universal device on said one part of the bone and said other part of the bone until they grow together naturally;

said adjustable means on said at least one elongated member for fixation or limited guided movement of said moveable holder on said at least one elongated member comprising a threaded end of said at least elongated member and two nuts screwed onto said threaded end on both sides of said moveable holder.

* * * * *